(12) United States Patent
Ridvan et al.

(10) Patent No.: US 8,071,791 B2
(45) Date of Patent: Dec. 6, 2011

(54) METHOD FOR THE PREPARATION OF (S)-N-METHYL-3-(1-NAPHTHYLOXY)-3-(2-THIENYL)PROPYLAMINE HYDROCHLORIDE (DULOXETINE)

(75) Inventors: Ludek Ridvan, Prague (CZ); Kamal Jarrah, Prague (CZ); Josef Cinibulk, Prague (CZ); Monika Zatopkova, Ostrava (CZ); Lukas Placek, Moravsky Kocov (CZ)

(73) Assignee: Zentiva k.s., Praha (CZ)

( * ) Notice: Subject to any disclaimer, the term of this patent is extended or adjusted under 35 U.S.C. 154(b) by 738 days.

(21) Appl. No.: 12/159,905

(22) PCT Filed: Dec. 22, 2006

(86) PCT No.: PCT/CZ2006/000096
§ 371 (c)(1),
(2), (4) Date: Jul. 2, 2008

(87) PCT Pub. No.: WO2007/076733
PCT Pub. Date: Jul. 12, 2007

(65) Prior Publication Data
US 2008/0293952 A1    Nov. 27, 2008

(30) Foreign Application Priority Data
Jan. 4, 2006 (CZ) .................... PV 2006-7

(51) Int. Cl.
*C07D 333/16* (2006.01)
(52) U.S. Cl. ....................................... 549/75
(58) Field of Classification Search ............. 549/75
See application file for complete search history.

(56) References Cited

U.S. PATENT DOCUMENTS
5,362,886 A    11/1994   Berglund
(Continued)

FOREIGN PATENT DOCUMENTS
EP         0 273 658         7/1988
(Continued)

OTHER PUBLICATIONS

Sorbera et al., "Duloxetine Oxalate", Drugs of the Future, Barcelona, ES, vol. 25, No. 9, 2000, pp. 907-916.
(Continued)

*Primary Examiner* — Taofiq A Solola
(74) *Attorney, Agent, or Firm* — Pearl Cohen Zedek Latzer, LLP

(57) ABSTRACT

A method of preparation of (S)-N-methyl-3-(1-naphthyloxy)-3-(2-mienyl)propylamine of Formula (I) and its pharmaceutically acceptable salts, comprising a) reaction of (RS)-N,N-dimethyl-3-(1-naphthyloxy)-3-(2-thienyl)propylamine with optically active D-tartaric acid or an acid salt derived from D-tartaric acid forming a mixture of diastereoisomeric salts of N,N-dimethyl-3-(1-naphthyloxy)-3-(2-thienyl)propylamine and D-tartaric acid (2:1), b) isolation of the salt (S)-N,N-dimethyl-3-(naphthyloxy)    -3-(2-thienyl)propylamine/D-tartrate (2:1) from the mixture of diastereoisomeric salts in an organic solvent, water or a mixture thereof and release of (S)-N,N-dimethyl-3-(1-naphthyloxy)-3-(2-thienyl)propylamine by action of an inorganic or organic base, c) demethylation of (S)-N,N-dimethyl-3-(1-naphthyloxy)-3-(2-thienyl)propylamine by action of an alkylchloroformate of formula ClCOOR (R=$C_1$-$C_5$ alkyl, or $C_6$-$C_{12}$ aryl or alkylraryl), especially phenyl, ethyl or methyl chloroformate, and d) hydrolytic release of the duloxetine base of formula I and optionally conversion of the base to a salt with the respective acid, or salt of a weak base.

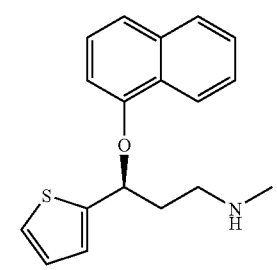

(I)

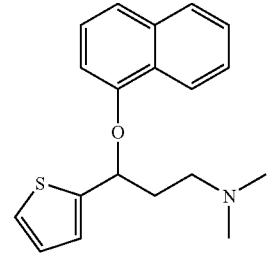

(III)

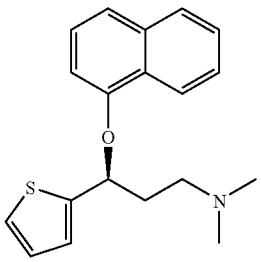

((S)-III)

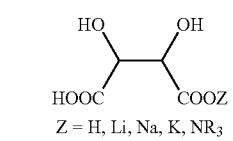

(IV)
Z = H, Li, Na, K, $NR_3$
R = H, C1-C7

8 Claims, No Drawings

U.S. PATENT DOCUMENTS

2003/0225153 A1  12/2003  Eckert et al.

FOREIGN PATENT DOCUMENTS

| WO | WO 2004/005239 | 1/2004 |
| WO | WO 2004/056795 | 7/2004 |
| WO | WO 2005/108386 | 11/2005 |
| WO | WO 2006/045255 | 5/2006 |
| WO | WO 2006/126213 | 11/2006 |

OTHER PUBLICATIONS

International Search Report for International Application No. PCT/CZ2006/000096 mailed Jun. 29, 2007.

METHOD FOR THE PREPARATION OF (S)-N-METHYL-3-(1-NAPHTHYLOXY)-3-(2-THIENYL)PROPYLAMINE HYDROCHLORIDE (DULOXETINE)

CROSS-REFERENCE TO RELATED APPLICATIONS

This application is a National Phase Application of PCT International Application No. PCT/CZ2006/000096, entitled "A METHOD FOR THE PREPARATION OF (S)-N-METHYL-3-(1-NAPHTHYLOXY)-3-(2-THIENYL)PROPYLAMINE HYDROCHLORIDE(DULOXETINE)", International Filing Date Dec. 22, 2006, published on Jul. 12, 2007 as International Publication No, WO 2007/076733, which in turn claims priority from Czechoslovakian Patent Application No. PV 2006-7, filed Jan. 4, 2006, both of which are incorporated herein by reference in their entirety.

TECHNICAL FIELD

The invention concerns a new method of preparation of (S)-N-methyl-3-(1-naphthyloxy)-3-(2-thienyl)propylamine of formula I

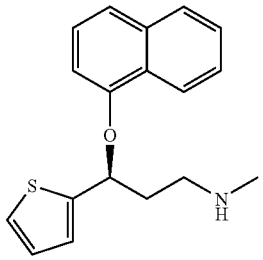

(I)

known under the generic name duloxetine, and its pharmaceutically acceptable salts.

BACKGROUND ART

Duloxetine is a selective serotonin and noradrenaline reuptake inhibitor, therapeutically useful to treat for example depression and urinary incontinence.

Preparation of Duloxetine and its Intermediate Products is Described for Example in patents EP 0 273 658, U.S. Pat. No. 5,362,886, WO 2004/005239, US 2003/0225153. The basic used reaction is described in the following scheme 1.

Scheme 1

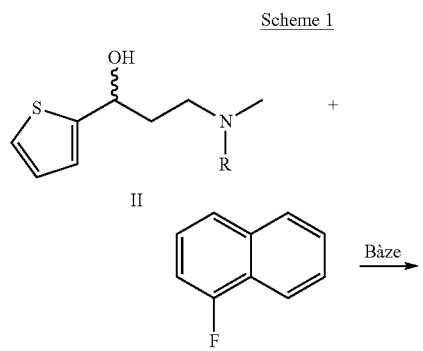

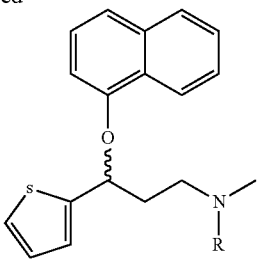

R = H, Me

Most of the syntheses uses for the reaction already optically active intermediate product of formula II, i.e. (S)-N,N-dimethyl-3-hydroxy-3-(2-thienyl)propylamine. In case of syntheses of many optically active substances, resolution or obtaining optically pure intermediates leads to better yields than resolving the final products. However, in case of duloxetine, it has turned out that when it is further treated according to Scheme 1 racemization takes place again. The final product obtained in this way is not, therefore, enantiomerically pure and it is necessary to recrystallize it again. Of course, this decreases the yield of the process.

A solution of undesirable racemization in the course of reaction according to Scheme 1 is offered by patent application WO 2004/056795 A1. The authors have chosen a method of preparation of racemic duloxetine and its resolving with a suitable chiral acid. Using this method, they, of course, prevent possible racemization; however, on the other hand, by also processing the undesirable (R)-enantiomer until the final stage they increase losses. In this application, di-p-toluoyltartaric acid is presented as the most suitable acid; in patent application WO 2005/108386 A1, use of one equivalent of this derivative of tartaric acid in resolving racemic duloxetine, i.e. 130 g for 100 g of the base, is mentioned in the Examples.

In the original patents, the reaction according to Scheme 1 was used as catalysts. These bases are relatively costly and when they are used it is necessary to avoid moisture, with which they can react violently.

Application WO 2004/056795 also publishes a method of performing reaction according to Scheme 1, where the use of a phase transfer catalyst allows for the reaction to proceed also with weaker bases such as alkali metal hydroxides.

According to our earlier invention (CZ patent 297560, WO 2006/045255) it is advantageous to use, for preparation of (S)-N-methyl-3-(1-naphthyloxy)-3-(2-thienyl)propylamine (duloxetine), the optically inactive (RS)-N,N-dimethyl-3-(1-naphthyloxy)-3-(2-thienyl)propylamine of formula III

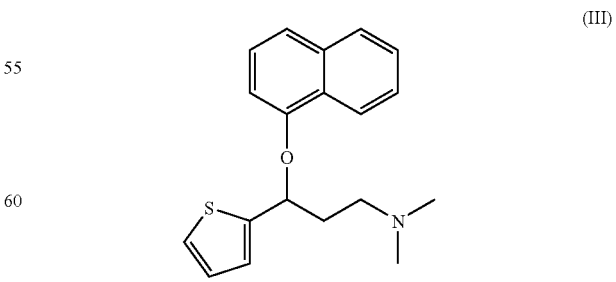

(III)

which is resolved using an optically active acid, preferably D-tartaric acid. The optically active acid is used in the stoichiometric ratio with respect to the substance of formula III.

The (S)-enantiomer, is isolated which is further demethylated using alkylchloroformates, whereupon hydrolysis is performed and the substance of formula I is isolated.

Preparation of the duloxetine salt is described in Example 2 (Method 2) of U.S. Pat. No. 5,362,886. The final product is obtained via reaction of concentrated hydrochloric acid with a solution of the duloxetine base in ethylacetate. An inoculating crystal of duloxetine hydrochloride is added to the acidified reaction mixture and the mixture is diluted with a further amount of ethylacetate; after 30 minutes of stirring, the mixture is re-concentrated to the initial volume and then stirred at ambient temperature for 1 hour and at the temperature 0° C. for 1 hour. However, when this procedure was reproduced it has turned out that the resulting duloxetine hydrochloride was not completely colorless but slightly pinkish to brownish, which can result in an impure product. The duloxetine molecule is relatively instable, especially in acidic environment. Considering that duloxetine hydrochloride is usually prepared via neutralization of the base with hydrochloric acid, the crude product can contain various impurities. The method of the final purification is, therefore, very important for obtaining the desired quality of the substance and the desired yield as well.

The present invention provides a complete and very advantageous solution of the preparation of duloxetine.

DISCLOSURE OF INVENTION

The invention concerns a new method of preparing (S)-N-methyl-3-(1-naphthyloxy)-3-(2-thienyl)propylamine of formula I (I)

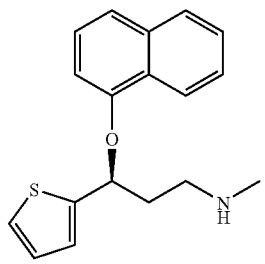

and its pharmaceutically acceptable salts, such as for example hydrochloride, which comprises resolving of (RS)-N,N-dimethyl-3-(1-naphthyloxy)-3-(2-thienyl)propylamine of formula III, (III)

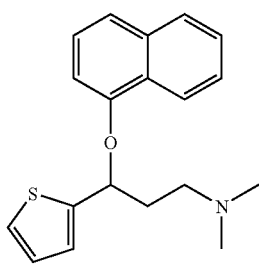

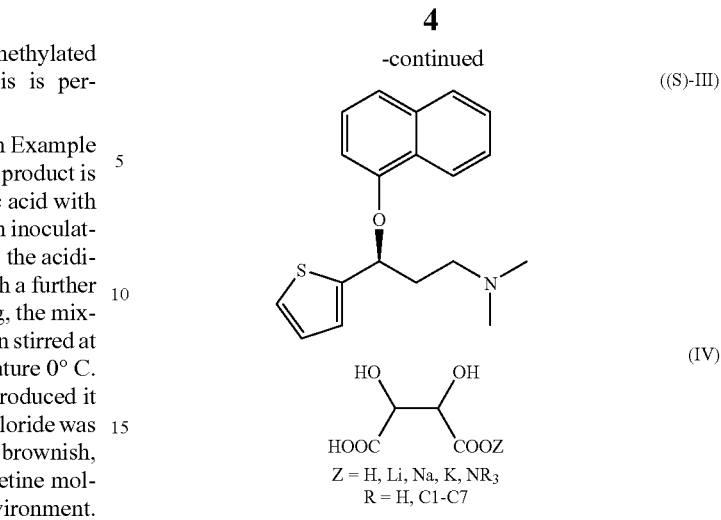

first by converting it to a mixture of diastereoisomeric salts of N,N-dimethyl-3-(naphthyloxy)-3-(2-thienyl)propylamine/D-tartrate via reaction with optically active tartaric acid in the molar ratio 1:2 relative to the substance of formula III or with optically active alkali metal tartrate or ammonium tartrate, or an alkylammonium tartrate, of formula IV, in the molar ratio 1:1, followed by isolating the salt (S)-N,N-dimethyl-3-(naphthyloxy)-3-(2-thienyl)propylamine/D-tartrate (2:1) (Scheme 2) from the mixture of the diastereoisomeric salts in an organic solvent, water or a mixture thereof.

Scheme 2

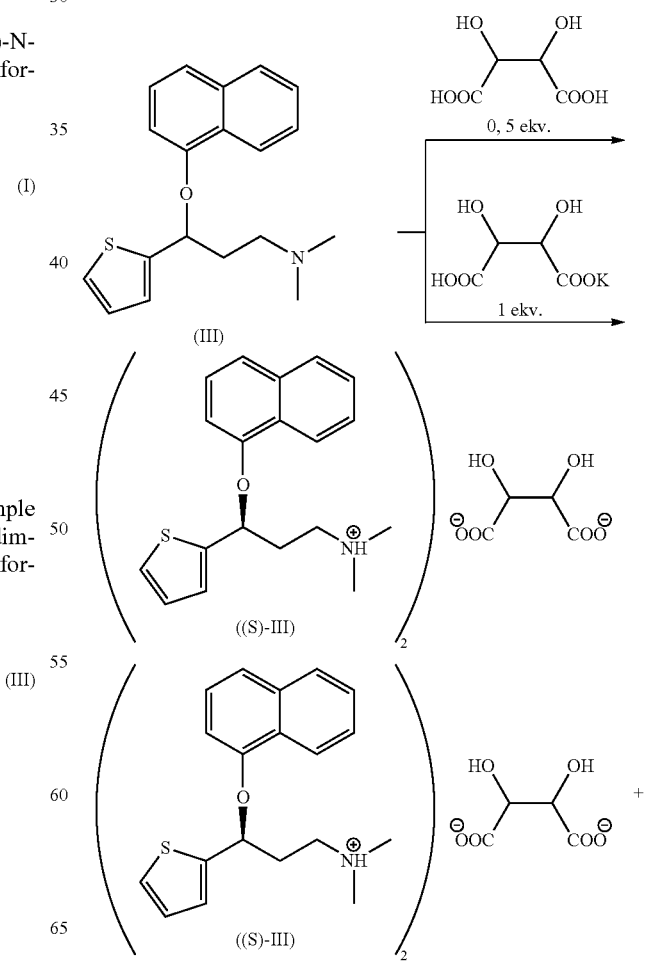

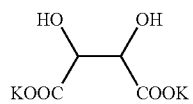

(S)-N,N-dimethyl-3-(1-naphthyloxy)-3-(2-thienyl)propylamine of formula (S)-(III) is then released from the salt (S)-N,N-dimethyl-3-(naphthyloxy)-3-(2-thienyl)propylamine/D-tartrate (2:1) by action of an inorganic or organic base, followed by demethylation with an alkylchloroformate of formula ClCOOR(R=$C_1$-$C_5$ alkyl, or $C_6$-$C_{12}$ aryl or alkylaryl), and, finally, by hydrolytically releasing the duloxetine base of formula I.

D-tartaric acid in combination with potassium (sodium, lithium) hydroxide, hydroxylamine or the respective alkylamine in an equimolar ratio to D-tartaric acid can be used in an equivalent manner instead of the tartrate.

The starting substance of formula III is prepared according to Scheme 1 via reaction of (RS)-N,N-dimethyl-3-hydroxy-3-(2-thienyl)propylamine with 1-fluornaphtalene in a solution of dimethylsulfoxide, at 80 to 150° C. in the presence of a base selected from carbonates, hydroxides or alcoholates of alkali metals. This arrangement allows for catalysis with a weaker base without use of phase-transfer catalysts.

An optically active acid is used for resolving (RS)-N,N-dimethyl-3-(1-naphthyloxy)-3-(2-thienyl)propylamine of formula III. According to the present invention, preferably 0.5 equivalent of D-tartaric acid or 1 equivalent of an alkali metal D-tartrate or ammonium D-tartrate, or alternatively alkylammonium tartrate of formula IV can be used. Monopotassium D-tartrate has turned out to be particularly advantageous. Advantages of the method of preparation according to the invention compared with using 1 equivalent of D-tartaric acid include:

(1) the salt can be easily prepared in an aqueous environment, especially in a mixture of water and a polar aprotic solvent (e.g. DMSO, DMF). According to a preferred embodiment, a polar aprotic solvent, e.g. dimethylsufoxide, is used as the reaction environment already during preparation of the compound of formula III, and after performing the reaction, the reaction mixture is only diluted with water (at least double amount (by volume) of water with respect to the polar aprotic solvent), 0.5 equivalent of tartaric acid or 1 equivalent of monopotassium tartrate is added, and after cooling, the precipitated salt is filtered off, which avoids laborious extraction of the base with an organic solvent, (2) better capacity to crystallize of the desired salt (S)-N,N-dimethyl-3-(naphthyloxy)-3-(2-thienyl)propylamine/D-tartrate (2:1), which leads to easier reproducibility of the resolution and also to higher optical purity of the obtained salt, (3) possibility to use easily regenerable monopotassium tartrate or only 0.5 equivalent of tartaric acid, which leads to lower expenses concerning raw materials and also lower amount of waste produced during preparation.

Using non-derivatized tartaric acid or its acidic salts is advantageous for the following reasons: (a) low molecular weight, which results in using lower amount of relatively expensive chiral agent (one needs, for 1 mole of base III, e.g., 75 g of tartaric acid (0.5 equivalent) or 188 g of monopotassium tartrate (1 equivalent) or 424 g of di-p-toluoyltartaric acid (1 equivalent)); (b) easy regeneration in the form of directly usable acid tartrate (during regeneration from aqueous liquors, after addition of 1 equivalent of a mineral acid, a very badly water-soluble acid tartrate (e.g. of monopotassium tartrate) crystallizes), In contrast, derivatives of tartaric acid based on esters, e.g. di-p-toluoyltartaric acid, are usually instable in a basic aqueous environment (possibility of hydrolysis); in addition, during regeneration from aqueous liquors it is usually necessary, after acidification, to make extraction with an organic solvent and crystallization.

The salt (S)-N,N-dimethyl-3-(naphthyloxy)-3-(2-thienyl)propylamine/D-tartrate (2:1) is isolated from the mixture of diastereoisomeric salts from a solvent from the group of aliphatic or cyclic ethers, e.g. tetrahydrofuran or diethylether, $C_3$-$C_6$ ketones, e.g. acetone, or lower alcohols, e.g. $C_1$-$C_3$ ones, or water, or a mixture of these solvents in an appropriate ratio, at temperatures from 0 to 80° C. An aqueous solution of THF containing from 0 up to 10% of water is preferably used.

(S)-N,N-dimethyl-3-(1-naphthyloxy)-3-(2-thienyl)propylamine of formula (S)-(III) is released from the salt (S)-N,N-dimethyl-3-(naphthyloxy)-3-(2-thienyl)propylamine/D-tartrate (2:1) by action of an inorganic or organic base in the environment of water and a water-immiscible organic solvent.

The prepared (S)-N,N-dimethyl-3-(1-naphthyloxy)-3-(2-thienyl)propylamine (S)-(III) is demethylated in the next step. Demethylation is performed by action of an alkyl or aryl chloroformate from the group of compounds for general formula ClCOOR, wherein R is selected from the group of $C_1$-$C_5$ alkyls or $C_6$-$C_{12}$ aryls or alkylaryls, in a solvent mixture of toluene and diisopropylethylamine at temperatures from 50 to 110° C., followed by hydrolysis with an alkali metal hydroxide.

The undesired (R)-N,N-dimethyl-3-(1-naphthyloxy)-3-(2-thienyl)propylamine can be returned to production process after it is racemized with an inorganic or organic base, e.g. potassium tert-butanolate, in an organic solvent environment, preferably in dimethylsulfoxide. After completion of the reaction, the mixture is diluted with water and enters to the process as a recycled portion along with the original raw material before resolving of racemic (RS)-N,N-dimethyl-3-(1-naphthyloxy)-3-(2-thienyl)propylamine of formula III into individual diastereoisomers.

The duloxetine base can be converted to any pharmaceutically acceptable salt. The hydrochloride and oxalate have been previously described, while the hydrochloride is commonly used for medical purposes.

A method of preparation of the hydrochloride salt from the duloxetine base represents another aspect of the present invention. Preparation of this salt is commonly performed via reaction of the duloxetine base with concentrated hydrochloric acid in ethylacetate environment. However, it has now turned out that substitution of ethylacetate by a lower ketone, such as for example ethylmethylketone, results in higher yields of higher quality duloxetine hydrochloride, especially when duloxetine hydrochloride is prepared and isolated via the method according to this invention. For comparison of effects of the used solvent on quality of the substance, we have used contaminated duloxetine hydrochloride that was obtained as the second fraction from mother liquors after their concentration. In Table 1, a HPLC print-out (C18 reverse column, mobile phase: water/acetonitrile, phosphate buffer pH 7.6) is presented showing analysis of the starting substance and then of the purified substance obtained after 1 hour refluxing in a six-fold amount of the solvent (i.e. 6 ml of the solvent for 1 g of the starting substance), cooling to ambient temperature, filtration and drying.

TABLE 1

Effect of used solvent on quality of the substance

| Impurity | Starting substance | Substance purified in ethylacetate | Substance purified in ethylmethylketone |
|---|---|---|---|
| RRT 0.28 | 0.26 % | 0.16 % | 0.09 % |
| RRT 0.53 | 0.54 % | 0.42 % | 0.38 % |
| RRT 0.88 | 0.42 % | 0.12 % | <0.05 % |
| RRT 1.05 | 0.40 % | 0.36 % | 0.30 % |
| RRT 1.27 | 0.44 % | 0.19 % | 0.11 % |
| RRT 1.68 | 0.15 % | 0.09 % | <0.05 % |
| RRT 2.24 | 0.08 % | <0.05 % | <0.05 % |
| RRT 2.29 | 0.07 % | <0.05 % | <0.05 % |
| RRT 3.17 | 0.61 % | 0.30 % | <0.05 % |
| Sum of impurities | 2.97 % | 1.64 % | 0.88 % |

It is apparent from the Table that the content of all impurities is lower in the case when a ketone, in this case ethylmethylketone, was used. It is, therefore, apparent that ketones are more suitable solvents for preparation of duloxetine hydrochloride than esters, such as for example ethylacetate, both during its preparation via neutralization of the base with hydrochloric acid and for its possible purification.

It can be expected that ketones will be more suitable solvents than esters also for preparation of other pharmaceutically acceptable salts of duloxetine such as for example hydrobromide and hydrogensulfate.

The invention is further illustrated in the following examples.

EXAMPLES

Example 1

(RS)-N,N-dimethyl-3-(naphthyloxy)-3-(2-thienyl) propylamine/D-tartrate

A mixture of N,N-dimethyl-3-hydroxy-3-(2-thienyl)propylamine (185 g, 1 mole), potassium hydroxide (112 g, 2 moles) and 1-fluoronaphthalene (146 g, 1 mole) in dimethylsulfoxide (1000 ml) is stirred at 110° C. for 2 hours. After cooling down to 20° C., the mixture is filtered, diluted with water (3 ), monopotassium D-tartrate (188 g, 1 mole) is added, and the mixture is stirred at 80° C. for 0.5 hour. After cooling down, the precipitated product is sucked off, washed with water and dried. Yield: 328 g (85%).

Example 2

(RS)-N,N-dimethyl-3-(naphthyloxy)-3-(2-thienyl) propylamine/D-tartrate

A mixture of N,N-dimethyl-3-hydroxy-3-(2-thienyl)propylamine (185 g, 1 mole), potassium hydroxide (112 g, 2 moles) and 1-fluoronaphthalene (146 g, 1 mole) in dimethylsulfoxide (1000 ml) is stirred at 110° C. for 2 hours. After cooling down to 20° C., the mixture is filtered, diluted with water (3 ), D-tartaric acid (75 g, 0.5 mole) is added and the mixture is stirred at 80° C. for 0.5 hour. After cooling down, the precipitated product is sucked off, washed with water and dried. Yield: 313 g (81%).

Example 3

(S)-N,N-dimethyl-3-(naphthyloxy)-3-(2-thienyl) propylamine/D-tartrate (RS)-N,N-dimethyl-3-(naphthyloxy)-3-(2-thienyl)propylamine/D-tartrate (773 g, 1 mole) is dissolved in warm tetrahydrofuran (1500 ml) with addition of water (40 ml). After cooling down to ambient temperature, the mixture is stirred for 24 h. The precipitated crystals are recrystallized once more in tetrahydrofuran (400 ml) with an addition of water (12 ml) following the same procedure. Yield: 170 g (22%). Optical purity: 99.5% ee (CE).

Example 4

(S)-N,N-dimethyl-3-(naphthyloxy)-3-(2-thienyl) propylamine/D-tartrate (RS)-N,N-dimethyl-3-(naphthyloxy)-3-(2-thienyl)propylamine/D-tartrate (773 g, 1 mole) is dissolved in THF (1500 ml) with an addition of water (40 ml) under reflux. After gradual cooling down to ambient temperature, diethylether (300 ml) is added drop-wise to the mixture over 6 hours. The precipitated crystals are sucked off and washed with THF. Yield: 232 g (30%). Optical purity: 93% ee (CE).

Example 5

(S)-N,N-dimethyl-3-(naphthyloxy)-3-(2-thienyl) propylamine hydrochloride (duloxetine)

Diisopropylethylamine (210 ml) is added to a solution of (S)-N,N-dimethyl-3-(1-naphthyloxy)-3-(2-thienyl)-propanamine (311 g; 99.6% ee) in toluene (1200 ml) and phenylchloroformate (150 ml) is then added at 60° C. After two hours of stirring at 80° C., the mixture is cooled down, shaken with a diluted solution of hydrochloric acid, water and a 2% solution of sodium hydrogencarbonate. The organic phase is dried with sodium sulfate and evaporated. The evaporation residue is dissolved in ethanol (300 ml) and a 5M solution of potassium hydroxide (400 ml) is added drop-wise under reflux. After two hours of refluxing, the mixture is evaporated to half the volume, diluted with water (1000 ml) and extracted with toluene (300 ml). The organic phase is dried with sodium sulfate and evaporated. The evaporation residue is dissolved in ethylmethylketone (300 ml) and concentrated HCl (1 mole), diluted with ethylmethylketone (300 ml), is added drop-wise at 0° C.; then the mixture is stirred for two hours. The precipitated crystals are then sucked off. Yield: 250 g (75%), m.p.: 167-169° C. Recrystallization from ethylmethylketone affords colorless crystalline duloxetine hydrochloride, m.p. 170.5-171.5° C. Optical purity: 99.9% ee (CE), chemical purity: 99.9% (HPLC).

The invention claimed is:
1. A method of preparation of (S)-N-methyl-3-(1-naphthyloxy)-3-(2-thienyl)propylamine of formula I

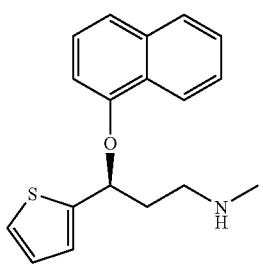

(I)

and its pharmaceutically acceptable salts, comprising
a) reaction of (RS)-N,N-dimethyl-3-(1-naphthyloxy)-3-(2-thienyl)propylamine of formula III

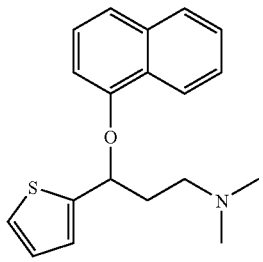

(III)

with optically active D-tartaric acid or an acid salt derived from D-tartaric acid forming a mixture of diastereoisomeric salts of N,N-dimethyl-3-(1-naphthyloxy)-3-(2-thienyl) propylamine and D-tartaric acid (2:1),
b) isolation of the salt (S)-N,N-dimethyl-3-(naphthyloxy)-3-(2-thienyl) propylamine/D-tartrate (2:1) from the mixture of diastereoisomeric salts in an organic solvent, water or a mixture thereof and release of (S)-N,N-dimethyl-3-(1-naphthyloxy)-3-(2-thienyl)propylamine of formula (S)-(III) by action of an inorganic or organic base

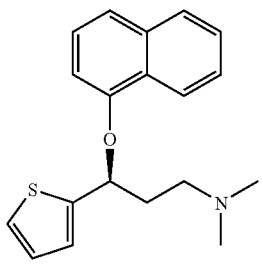

((S)-III)

c) demethylation of (S)-N,N-dimethyl-3-(1-naphthyloxy)-3-(2-hienyl)propylamine by action of an alkylchloroformate of formula ClCOOR, wherein R is a $C_1$-$C_5$ alkyl, or $C_6$-$C_{12}$ aryl or alkylaryl, and d) hydrolytic release of the duloxetine base of formula I and optionally conversion of the base to a salt with the respective acid, or salt of a weak base,
wherein the optically active substance in step (a) is D-tartaric acid in the molar ratio 1:2 relative to the substance of formula III, an alkali metal acid D-tartrate, ammonium tartrate, or alkylammonium tartrate of formula IV

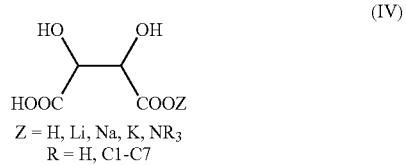

(IV)

$Z = H, Li, Na, K, NR_3$
$R = H, C1-C7$ in the molar ratio 1:1 relative to the substance of formula III.

2. The method according to claim 1, wherein the reaction in step a) is performed in the presence of water.

3. The method according to claim 2, wherein the reaction is performed in a solvent mixture composed of water and a polar aprotic solvent in a 2-fold to 10-fold (by volume) excess of water relative to the polar aprotic solvent.

4. The method according to claim 3, wherein the polar aprotic solvent is dimethylsulfoxide.

5. The method according to claim 1, wherein one uses, in step (b), for isolation of the salt (S)-N,N-dimethyl-3-(naphthyloxy)-3-(2-thienyl)propylamine/D-tartrate (2:1) from the mixture of diastereoisomeric salts, a solvent selected from the group of aliphatic and cyclic ethers, $C_3$-$C_6$ ketones, $C_1$-$C_3$ alcohols and water, or a mixture therof, and a temperature of from 0 to 80° C.

6. The method according to claim 5, wherein the solvent is an aqueous solution of THF containing from 0 to 10% of water.

7. The method according to claim 1, wherein in step (d), the substance of formula I is converted to its hydrochloride via reaction with hydrochloric acid in an environment of the solvent ethylmethylketone and the obtained duloxetine hydrochloride is crystallized from said solvent.

8. The method according to claim 1, wherein R is phenyl, ethyl or methyl.

* * * * *